(12) United States Patent
Karp et al.

(10) Patent No.: US 7,010,964 B2
(45) Date of Patent: Mar. 14, 2006

(54) PRESSURIZED MICROFLUIDIC DEVICES WITH OPTICAL DETECTION REGIONS

(75) Inventors: Christoph D. Karp, Pasadena, CA (US); Paren P. Patel, Sierra Madre, CA (US)

(73) Assignee: Nanostream, Inc., Pasadena, CA (US)

( * ) Notice: Subject to any disclaimer, the term of this patent is extended or adjusted under 35 U.S.C. 154(b) by 152 days.

(21) Appl. No.: 10/697,923

(22) Filed: Oct. 29, 2003

(65) Prior Publication Data

US 2004/0118189 A1 Jun. 24, 2004

Related U.S. Application Data

(60) Provisional application No. 60/423,196, filed on Oct. 31, 2002.

(51) Int. Cl.
*G01N 30/00* (2006.01)

(52) U.S. Cl. ..................................... 73/61.52; 73/61.57
(58) Field of Classification Search ............... 73/61.52, 73/61.53, 61.56, 61.57, 61.58, 61.61; 356/409, 356/410
See application file for complete search history.

(56) References Cited

U.S. PATENT DOCUMENTS

| | | | |
|---|---|---|---|
| 3,449,938 A | | 6/1969 | Giddings |
| 4,137,161 A | * | 1/1979 | Shimada et al. ............ 210/659 |
| 4,165,219 A | * | 8/1979 | Huber ........................ 436/161 |
| 5,303,021 A | | 4/1994 | Kita ............................ 356/72 |
| 5,376,252 A | | 12/1994 | Ekström et al. |
| 5,480,614 A | | 1/1996 | Kamahori |
| 5,571,410 A | | 11/1996 | Swedberg et al. |
| 5,595,650 A | | 1/1997 | Manz |
| 5,658,413 A | | 8/1997 | Kaltenbach et al. |

(Continued)

FOREIGN PATENT DOCUMENTS

| | | |
|---|---|---|
| EP | 1 106 244 A2 | 6/2001 |
| WO | WO 98/04909 | 2/1998 |
| WO | WO 98/45693 | 10/1998 |
| WO | WO 99/19717 | 4/1999 |
| WO | WO 99/33559 | 7/1999 |
| WO | WO 99/44217 | 9/1999 |
| WO | WO 00/21659 | 4/2000 |
| WO | WO 00/31528 | 6/2000 |
| WO | WO 00/72970 A1 | 12/2000 |
| WO | WO 01/38865 A1 | 5/2001 |
| WO | WO 03/101591 A1 | 12/2003 |

OTHER PUBLICATIONS

Ericson, Christer, et al., *Electroosmosis– and Pressure–Driven Chromatography in Chips Using Continuous Beds*, "Analytical Chemistry," vol. 72, No. 1, Jan. 1, 2000, pp. 81–87.

Ehrfeld, W., et al. *Potentials and Realization of Microreactors*, "DECHEMA Monographs," vol. 132, 1996.

(Continued)

*Primary Examiner*—Michael Cygan
(74) *Attorney, Agent, or Firm*—Vincent K. Gustafson (57) ABSTRACT

Microfluidic analytical devices and systems have at least one porous element disposed downstream of one or more optical detection regions in a pressure-based separation system. A porous element elevates the backpressure within an optical detection region, thus suppressing bubble formation and enhancing optical detection. Various types of porous elements include porous membranes, packed particulate material, and polymerized monoliths. Preferred devices may be fabricated with substantially planar device layers, including stencil layers, that are directly bonded without adhesives to form a substantially sealed microstructure suitable for performing pressure-based chromatographic separations at elevated operating pressures and with organic solvents.

23 Claims, 5 Drawing Sheets

U.S. PATENT DOCUMENTS

| | | | |
|---|---|---|---|
| 5,698,299 | A | 12/1997 | Schmidt et al. |
| 5,744,366 | A | 4/1998 | Kricka et al. ............... 436/63 |
| 5,757,482 | A | 5/1998 | Fuchs et al. ............... 356/246 |
| 5,846,396 | A | 12/1998 | Zanzucchi et al. .......... 204/601 |
| 5,863,502 | A | 1/1999 | Southgate et al. ............ 422/58 |
| 5,876,675 | A | 3/1999 | Kennedy ..................... 422/99 |
| 5,922,591 | A | 7/1999 | Anderson et al. ........ 435/287.2 |
| 5,922,604 | A | 7/1999 | Stapleton et al. ............. 436/46 |
| 6,074,725 | A | 6/2000 | Kennedy ................... 428/188 |
| 6,235,471 | B1 | 5/2001 | Knapp et al. .................. 435/6 |
| 6,261,430 | B1 | 7/2001 | Yager et al. ................ 204/455 |
| 6,274,089 | B1 | 8/2001 | Chow et al. ............... 422/101 |
| 6,274,726 | B1 | 8/2001 | Lagharn, Jr. et al. .... 536/25.4 |
| 6,293,012 | B1 | 9/2001 | Moles ................... 29/890.124 |
| 6,444,461 | B1 | 9/2002 | Knapp et al. ............ 435/283.1 |
| 6,491,816 | B1 | 12/2002 | Petro ...................... 210/198.2 |
| 6,494,230 | B1 | 12/2002 | Chow ........................ 137/827 |
| 6,494,614 | B1 | 12/2002 | Bennett et al. ............. 366/336 |
| 6,499,337 | B1 * | 12/2002 | Hoffman .................... 73/61.72 |
| 6,532,978 | B1 | 3/2003 | Müller-Kuhrt et al. ........ 137/1 |
| 6,533,840 | B1 | 3/2003 | Martin et al. .................. 95/45 |
| 6,537,501 | B1 | 3/2003 | Holl et al. .................. 422/101 |
| 6,537,506 | B1 | 3/2003 | Schwalbe et al. ........... 422/130 |
| 6,569,325 | B1 | 5/2003 | Yan ........................ 210/198.2 |
| 6,581,441 | B1 | 6/2003 | Paul ......................... 73/61.52 |
| 6,607,907 | B1 | 8/2003 | McNeely et al. ........ 435/286.6 |
| 6,814,859 | B1 * | 11/2004 | Koehler et al. .......... 210/198.2 |
| 6,848,462 | B1 * | 2/2005 | Covington et al. ...... 137/15.01 |
| 2002/0189947 | A1 | 12/2002 | Paul et al. .................. 204/461 |
| 2003/0089663 | A1 | 5/2003 | Petro et al. ................ 210/656 |
| 2003/0094415 | A1 | 5/2003 | Tanimura ................... 210/656 |
| 2003/0118486 | A1 | 6/2003 | Zhou et al. ................ 422/102 |
| 2003/0168392 | A1 | 9/2003 | Masuda et al. .......... 210/198.2 |
| 2003/0187011 | A1 | 10/2003 | Lashuel et al. ............. 514/284 |
| 2003/0230524 | A1 * | 12/2003 | Soga et al. ............... 210/198.2 |

OTHER PUBLICATIONS

Ngola, Sarah M., et al., *Conduct-as-Cast Polymer Monoliths as Separation Media for Capillary Electrochromatography*, "Analytical Chemistry," vol. 73, No. 5, Mar. 1, 2001, pp. 849–856.

Shediac, Renée, et al., *Reversed-phase electrochromatography of amino acids and peptides using porous polymer monoliths*, "Journal of Chromatography A," 925, (2001), pp. 251–263.

Monahan, Jennifer, et al., *A Method for Filing Complex Polymeric Microfluidic Devices and Arrays*, "Analytical Chemistry," vol. 73, No. 13, Jul. 1, 2001, pp. 3193–3197.

Jacobson, Stephen C., et al., *Integrated Microdevice for DNA Restriction Fragment Analysis*, "Analytical Chemistry," vol. 68, No. 5, Mar. 1, 1996, pp. 720–723.

Ocvirk, Gregor, et al., *High Performance Liquid Chromatography Partially Integrated onto a Silicon Chip*, "Analytical Methods and Instrumentation," vol. 2, No. 2, (1995), pp. 74–82.

Manz, Andreas, et al., *Miniaturization of Separation Techniques Using Planar Chip Technology*, "Journal of High Resolution Chromatography," vol. 16, Jul. 26, 1993.

Cannon, Donald M., Jr., "Characterization of Molecular Transport within Gateable Nanofluidic Interconnects for Three-Dimensional Microfluidic Systems," *Micro Total Analysis Systems*, J.M. Ramsey and A. van den Berg (eds.), 2001 Kluwer Academic Publishers, The Netherlands, pp. 199–200.

* cited by examiner

PRESSURIZED MICROFLUIDIC DEVICES WITH OPTICAL DETECTION REGIONS

STATEMENT OF RELATED APPLICATION(S)

This application claims priority to commonly assigned U.S. Provisional Application Ser. No. 60/423,196, filed Oct. 31, 2002.

FIELD OF THE INVENTION

The present invention relates to systems for performing pressure-driven separation, such as high performance liquid chromatography.

BACKGROUND OF THE INVENTION

There has been a growing interest in the application of microfluidic systems to a variety of technical areas, including such diverse fields as biochemical analysis, medical diagnostics, analytical chemistry, chemical synthesis, and environmental monitoring. Microfluidic systems provide certain advantages in acquiring chemical and biological information. For example, microfluidic systems permit complicated processes to be carried out using very small volumes of fluid, thus minimizing consumption of both samples and reagents. Chemical and biological reactions occur more rapidly when conducted in microfluidic volumes. Furthermore, microfluidic systems permit large numbers of complicated biochemical reactions and/or processes to be carried out, either in parallel or in series, within a small area (such as within a single integrated device) and also facilitate the use of common control and interface components.

Among the various branches of analytical chemistry, the field of chromatography stands to particularly benefit from the application of microfluidic technology due to higher efficiency and increased throughput, such as may be afforded by performing multiple analyses in parallel in a miniaturized format. Chromatography encompasses a number of methods that are used for separating closely related components of mixtures. In fact, chromatography has many applications including separation, identification, purification, and quantification of compounds within various mixtures.

Liquid chromatography is a physical method of separation wherein a liquid "mobile phase" (typically consisting of one or more solvents) carries a sample containing multiple constituents or species through a "stationary phase" material (e.g., packed particles having functional groups and disposed within a tube) commonly referred to as a "separation column.") A sample is supplied to a separation column (stationary phase material) and carried by the mobile phase. As the sample solution flows within the mobile phase through the stationary phase, components of the sample solution will migrate according to interactions with the stationary phase and these components are retarded to varying degrees. The time a particular component spends in the stationary phase relative to the fraction of time it spends in the mobile phase will determine its velocity through the column. Following chromatographic separation in the column, the resulting eluate stream (consisting of mobile phase and sample components) contains a series of regions having elevated concentrations of individual species, which can be detected by various techniques to identify and/or quantify the species.

Although pressure-driven flow or electrokinetic (voltage-driven) flow can be used in liquid chromatography, pressure-driven flow is desirable since it permits a wider range of samples and solvents to be used and it avoids problems associated with high voltage systems (such as hydrolysis, which can lead to detrimental bubble formation). Within pressure-driven systems, higher pressures generally provide greater separation efficiencies. In conventional high performance liquid chromatography ("HPLC") systems, pressures of several hundred to thousands of pounds per square inch (psi) are commonly used with densely packed separation columns to provide increased separation efficiency and reduced separation times. A standard liquid chromatography column for performing HPLC has a tubular column body (typically steel, although materials like glass, fused silica, and/or PEEK are also used) and a high precision internal bore containing packed (particulate) stationary phase material, with the tube bounded at either end with fine filters or "frits" and end fittings. Samples are separated serially (i.e., one at a time) in conventional columns, which are re-used several times (and flushed between each use) before they become so contaminated that their effectiveness is diminished.

Typically, eluate from a separation column will be subjected to one or more analytical processes, including, but not limited to, optical detection, such as ultraviolet/visible ("UV/Vis") light absorbance or refractive index detection. To facilitate optical detection, a flow cell having optical windows and an eluate path therethrough is disposed downstream of the chromatography column, with fluid connections made by way of threaded fittings. A common problem that can interfere with post-column optical detection in HPLC systems, however, is the formation of bubbles in the detection region. Such bubbles are formed as gases dissolved in the mobile phase expand downstream of the column in the lower pressure environment of a flow cell, often causing baseline noise and drift. To mitigate such problems, conventional HPLC systems utilize solvent degassers upstream of a separation column to reduce the presence of gas in mobile phase, and further employ means to increase the backpressure in a detection region (such as a flow cell) downstream of the separation column.

Two general approaches are used to increase backpressure in a detection region: either providing a backpressure regulator (valve) or providing a capillary restrictor (tube) of appropriate length downstream of the detection region. Backpressure regulators are advantageously capable of providing a constant backpressure in a detection region over a range of different operating pressures. The utility of such regulators is limited, however, because they are expensive and require multiple parts that may reduce their reliability. Such regulators are typically characterized by non-negligible internal dead volume, which may "smear" or otherwise distort bands of species flowing therethrough, thus limiting the ability to perform further desirable analytical techniques (such as, for example, mass spectrometry) downstream of the optical detection region. Additionally, due to their expense and size, it would be difficult and/or impractical to use conventional HPLC backpressure regulators with highly parallel microfluidic separation systems.

The second conventional approach to elevating backpressure, providing a capillary tube downstream of an optical detection region, is inexpensive and involves no moving parts. But the utility of capillary restrictors is also limited due to packaging constraints and other concerns. To provide a desired backpressure, a capillary of appropriate size should be selected for a specific column exit condition (i.e., pressure and flow rate). Backpressure is generally increased by reducing the inner diameter of a capillary (but exceedingly small capillaries can become clogged) and/or increasing the length of the capillary (but very long capillaries can interfere with packaging constraints). In highly parallel microfluidic separation systems, it may be very cumbersome to provide one capillary restrictor for each separate detection region due to packaging constraints and the difficulty of making a large number of reliable, fluid-tight connections to small-bore capillary tubes.

In light of the foregoing, it would be desirable to provide a separation device having an optical detection region with compact means for elevating backpressure within the detection region. It would be further desirable for such a system to be inexpensive and easy to fabricate, with a minimum of moving parts to promote reliable, leak-free operation.

DETAILED DESCRIPTION OF PREFERRED EMBODIMENTS OF THE INVENTION

Definitions

The term "channel" as used herein is to be interpreted in a broad sense. Thus, it is not intended to be restricted to elongated configurations where the transverse or longitudinal dimension greatly exceeds the diameter or cross-sectional dimension. Rather, this term is meant to comprise cavities or tunnels of any desired shape or configuration through which liquids may be directed. A channel may be substantially filled or may contain internal structures comprising, for example, valves, filters, stationary phase media, and similar or equivalent components and materials.

The terms "column", "separation column", and "separation channel" as used herein are used interchangeably and refer to a region of a fluidic device that contains stationary phase material and is adapted to perform a separation process.

The term "interpenetrably bound" as used herein refers to the condition of two adjacent polymer surfaces being bound along a substantially indistinct interface resulting from diffusion of polymer chains from each surface into the other.

The term "microfluidic" as used herein refers to structures or devices through which one or more fluids are capable of being passed or directed and having at least one dimension less than about 500 microns.

The term "plurality" as used here refers to a quantity of two or more.

The term "stencil" as used herein refers to a material layer or sheet that is preferably substantially planar through which one or more variously shaped and oriented portions have been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between other layers such as substrates or other stencils.

The term "substantially metal-free" as used herein means substantially free of metals, metal ions, and organometallic compounds.

The term "substantially sealed" as used herein refers to the condition of having a sufficiently low unintended leakage rate and/or leakage volume under given flow, fluid identity, or pressure conditions. Types of unintended leakage include leakage or pooling that accumulates in unintended regions between device layers and leakage to an environment outside a microfluidic device. A substantially sealed microstructure is contemplated to have one or more fluidic ports or apertures to provide desirable fluidic inlet or outlet utility.

Microfluidic Devices Generally

Devices according to the present invention are preferably microfluidic devices defining internal channels or other microstructures having at least one dimension smaller than about 500 microns. Preferably, these microfluidic devices are constructed using stencil layers or sheets to define channels and/or chambers. As noted previously, a stencil layer is preferably substantially planar and has a channel or chamber cut through the entire thickness of the layer to permit substantial fluid movement within the stencil layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely-dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permit robust devices to be fabricated quickly and inexpensively compared to other conventional microfluidic fabrication technologies, such as surface micromachining or material deposition techniques.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers are intended to mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. In certain examples, particularly preferable materials include those that are substantially optically transmissive to permit viewing and/or electromagnetic analyses of fluid contents within a microfluidic device. Various examples may utilize porous materials, including filter materials, for device layers. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties.

Various means may be used to seal or bond layers of a device together, preferably to construct a substantially sealed structure. For example, adhesives may be used. In one example, one or more layers of a device may be fabricated from single- or double-sided adhesive tape, although other methods of adhering stencil layers may be used. A portion of the tape (of the desired shape and dimensions) can be cut and removed to form channels, chambers, and/or apertures. A tape stencil can then be placed on a supporting substrate with an appropriate cover layer, between layers of tape, or between layers of other materials. In one example, stencil layers can be stacked on each other. In this example, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an example. Suitable tape carrier materials include but are not limited to polyesters, polycarbonates, polytetrafluoroethlyenes, polyolefins (including polypropylenes and polyethylenes), and polyimides. Such tapes may have various methods of curing, including curing by pressure, temperature, or chemical or optical interaction. The thicknesses of these carrier materials and adhesives may be varied.

In another example, device layers may be directly bonded without using adhesives to provide high bond strength (which is especially desirable for high-pressure applications) and eliminate potential compatibility problems between such adhesives and solvents (particularly organic solvents) and/or samples. Specific examples of adhesiveless methods for directly bonding layers of non-biaxially-oriented polypropylene to form stencil-based microfluidic structures are disclosed in commonly assigned U.S. patent application Ser. No. 10/313,231, filed Dec. 6, 2001, which is hereby incorporated by reference as if set forth fully herein.

In one embodiment disclosed therein, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded, substantially sealed microstructure with adjacent layers interpenetrably bound together, with the resulting device being well-suited for use with high-pressure fluidic processes. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices. The use of polypropylene is particularly preferred for its inertness and favorable optical properties (e.g., it is a substantially optically transmissive material).

It is desirable to avoid the use of metals, metal ions, and other organometallic bonding agents within a microfluidic chromatography device for performing adhesiveless bonding methods, since metals can contaminate stationary phase material, thus rendering the stationary phase material incapable of performing its intended separation of a sample. Additionally, many mobile phase solvents will cause leaching of metal ions into the mobile phase, thus causing detection problems such as extraneous peaks and/or signal drift. Accordingly, preferred devices provided herein are substantially metal-free.

Further examples of microfluidic devices may be fabricated from various materials using well-known techniques such as embossing, stamping, molding, and soft lithography.

Microfluidic channels can also be packed with stationary phase material to yield columns suitable for high pressure liquid chromatography. In preferred examples, multiple columns are integrated into a single microfluidic device to accomplish simultaneous separation of multiple samples in parallel. Representative devices and packing methods are disclosed in commonly assigned U.S. patent application Ser. No. 10/366,985, filed Feb. 13, 2003, which is hereby incorporated by reference as if set forth fully herein.

Preferred Microfluidic Separation Devices

Figure 1A:
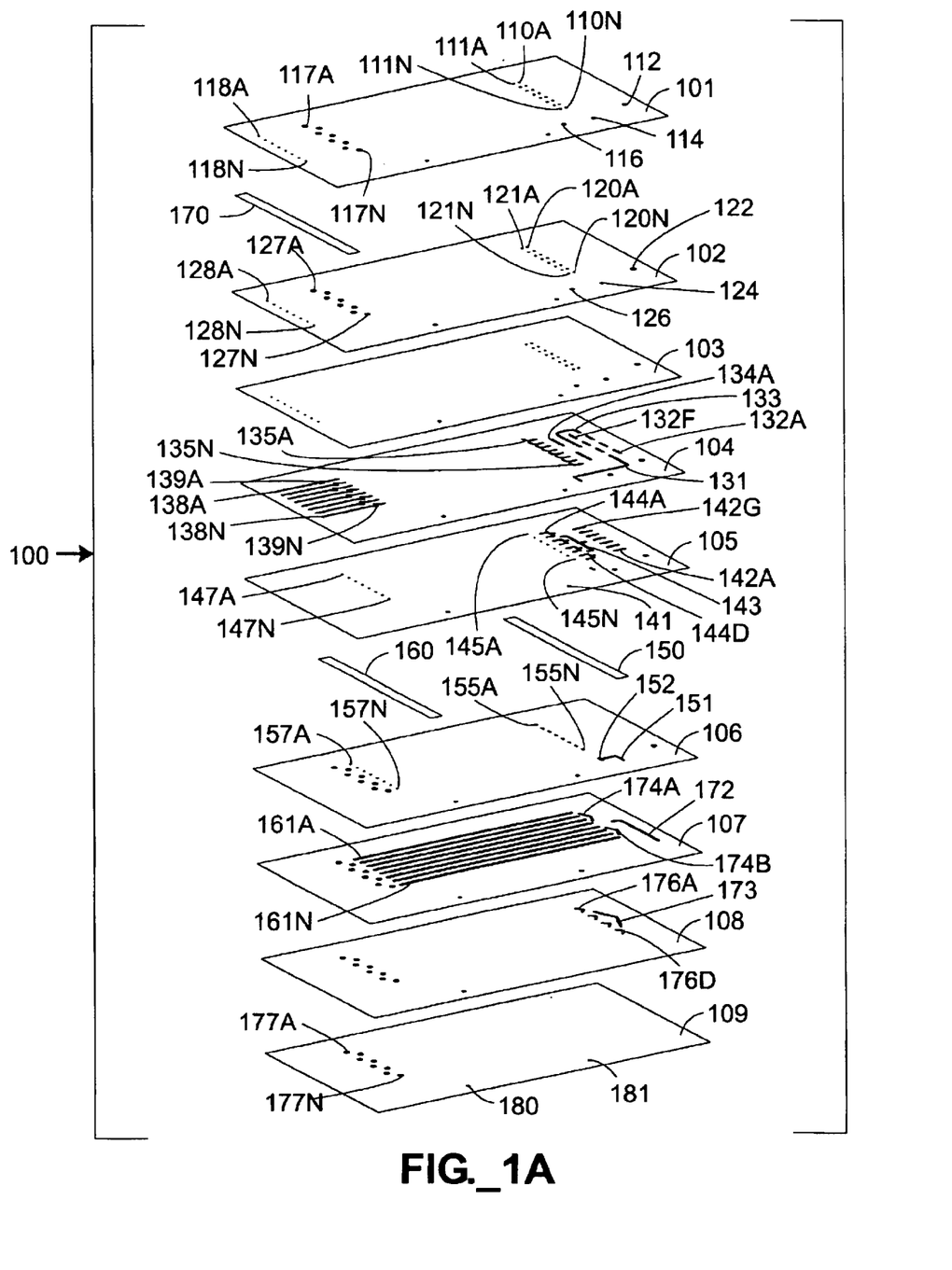
FIG. 1A is an exploded perspective view of a multi-layer pressure-driven microfluidic device having multiple separation columns, optical detection regions disposed downstream of the columns, and a porous membrane disposed downstream of the optical detection regions.
Figure 1B:
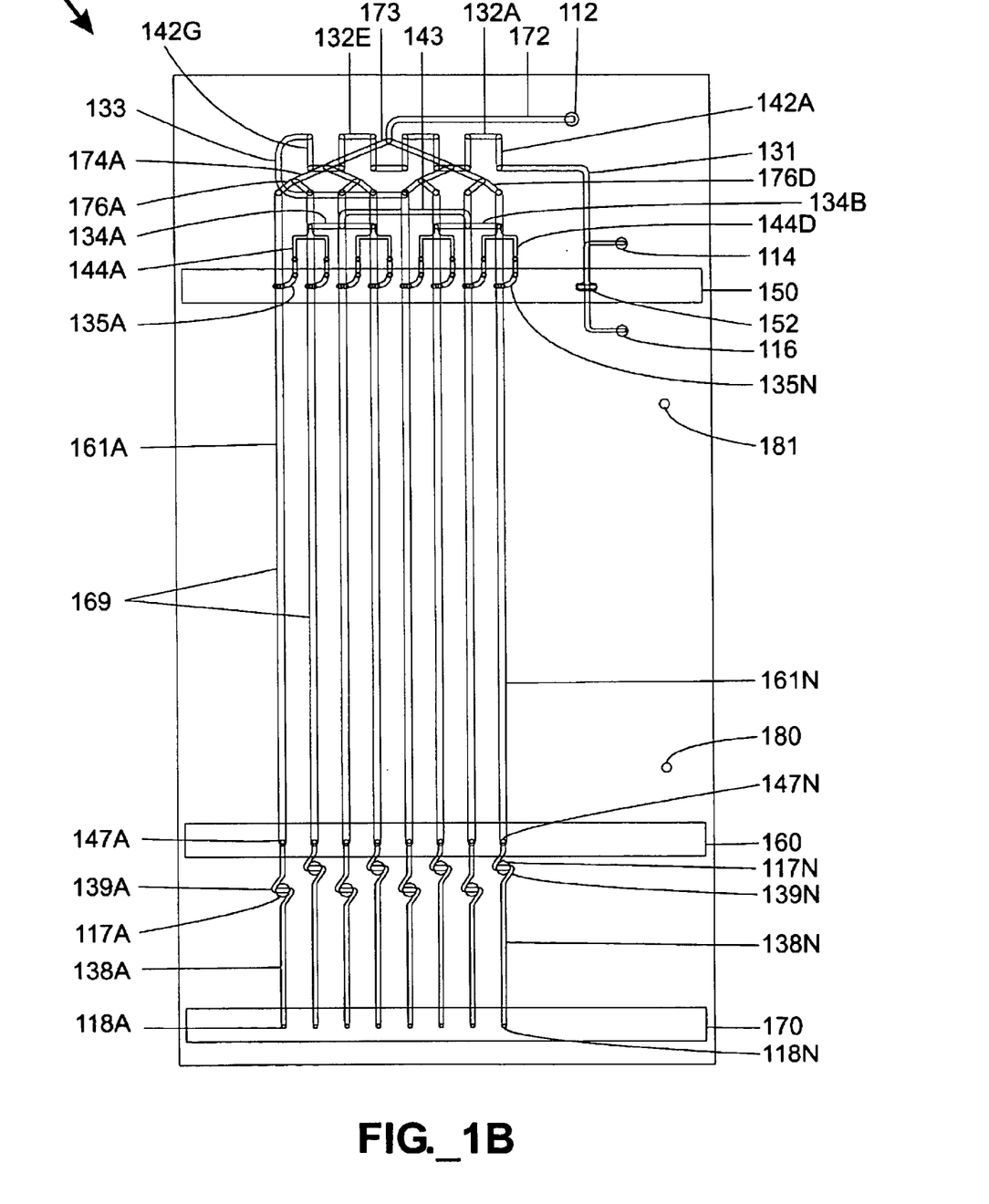
FIG. 1B is a simplified top view of the assembled device of FIG. 1A.
Figure 1C:
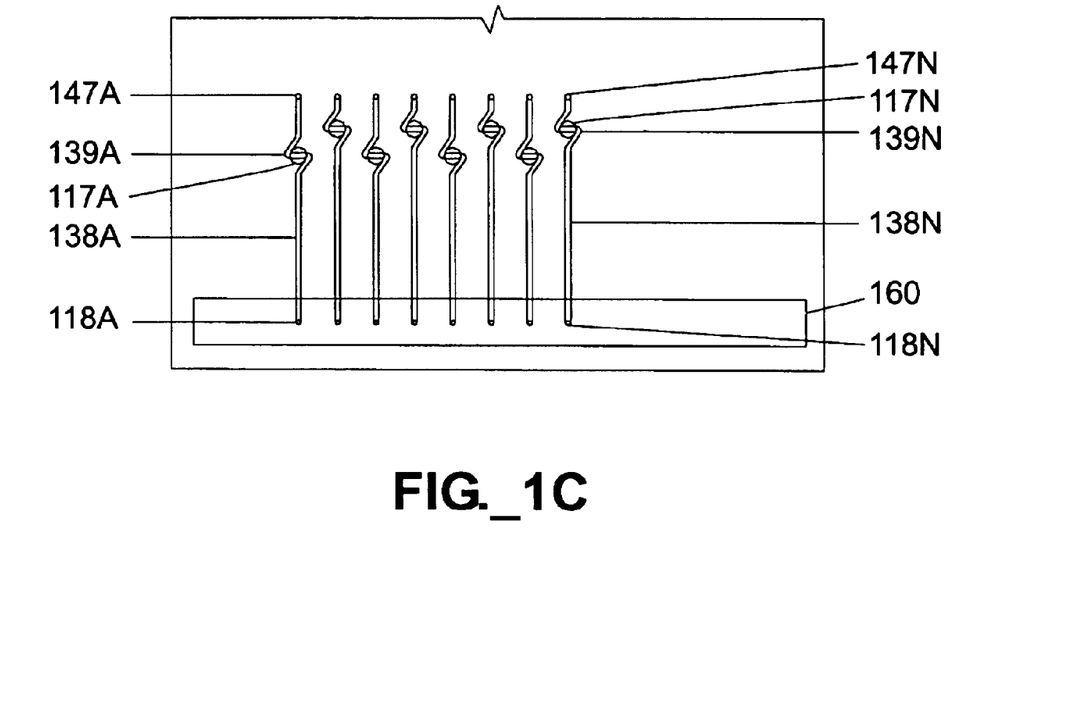
FIG. 1C is an expanded top view of a portion of the device of FIGS. 1A–1B, the view including the optical detection regions and downstream porous membrane, but omitting other elements for clarity.

In a preferred embodiment, a pressure-driven microfluidic separation device includes multiple separation columns, optical detection regions disposed downstream of each column, and a porous membrane disposed downstream of the optical detection regions. One advantage of providing multiple columns in a single microfluidic device is that multiple (different) samples may be separated and analyzed simultaneously using common and/or a minimum number of expensive system components such as pumps, pulse dampers, etc. For example, FIGS. 1A–1C illustrate a pressure-driven microfluidic separation device 100 including eight separation channels 161A–161N, eight optical detection regions 139A–139N, and a single porous membrane 170 disposed downstream of the optical detection regions 139A–139N. (Although FIGS. 1A–1C depict the device 100 having eight columns 161A–161N and eight optical detection regions 139A–139N, it will be readily apparent to one skilled in the art that any number of columns 161A–161N and associated optical detection regions 139A–139N may be provided. For this reason, the designation "N" is used to represent the last column 161N and the last detection region 139N, with the understanding that "N" represents a variable and could represent any desired number of columns or detection regions. This convention is used throughout this document.)

The device 100 may be constructed with nine device layers 101–109, including multiple stencil layers 104–108. Each of the nine layers 101–109 defines two alignment holes 180, 181, which may be used in conjunction with fixed external pins (not shown) to aid in aligning the layers 101–109 during construction and/or to aid in aligning the device 100 with an external interface such as a mechanical seal (not shown) or slurry packing apparatus (not shown).

The first layer 101 defines several fluidic ports: three solvent inlet ports 112, 114, 116 that may be used to admit mobile phase solvent to the device 100; eight pairs of sample ports 111A–110N and 111A–111N that permit samples to be supplied to sample loading segments 135A–135N (defined in the fourth layer 104); and eight outlet ports 118A–118H to permit mobile phase and separated sample species to exit the device 100 downstream of the optical detection regions 139A–139N and porous membrane 170. Due to the sheer number of elements depicted in FIGS. 1A–1B, numbers for selected elements within alphanumeric series groups (e.g., sample ports 110B–110G, 111B–111G, sample loading segments 135B–135G, outlet ports 118B–118G) are omitted for clarity. Notably, of the three solvent inlet ports 112, 114, 116, the first solvent inlet port 112 is additionally used to admit slurry to the device 100 during a column packing procedure. The first layer 101 further defines eight apertures 117A–117N that, along with identical apertures 127A–127N defined in the second layer 102 and apertures 177A–177N defined in the sixth through ninth device layers 106–109, facilitate optical detection by locally reducing the thickness of material bounding (from above and below) the detection regions 139A–139H of channels 138A–138H defined in the fourth layer 103.

The second through sixth layers 102–106 each define a first solvent via 122 for communicating a mobile phase solvent from a first mobile phase inlet port 112 to a transverse channel 172 defined in the seventh layer 107. A second solvent via 124 is defined in each of the second through fifth device layers 102–105 for communicating a mobile phase solvent from the second mobile phase inlet port 114 to a channel segment 151 defined in the sixth layer 105. A third solvent via 126 is defined in the second and third layers 102, 103 to communicate a mobile phase solvent from the third mobile phase inlet port 116 to an initial solvent mixing channel 131 defined in the fourth layer 104. Eight pairs of sample vias 120A–120N and 121A–121N defined in the second and third layers 102, 103 are interposed between the sample ports 110A–110N, 111A–111N and the sample loading segments 135A–135N defined in the fourth layer 104. Additionally, eight eluate vias 128A–128N are defined in the third and fourth layers 103, 104 and interposed between the outlet ports 118A–118N and the outlet channels 138A–138H defined in the fourth layer 104.

The fourth layer 104 defines a series of six transverse segments 132A–132F and a curved channel 133. The transverse segments 132A–132F and curved channel 133, when coupled with the longitudinal (parallel) segments 142A–142G defined in the fourth layer 104, form continuous flow path between the initial solvent mixing channel 131 defined in the fourth layer 104 and a large forked channel 143 defined in the fifth layer 105. The fourth layer 104 also defines two transverse segments 134A, 134B that fluidically couple the large forked channel 143 to four small forked channels 144A–144D defined in the fifth layer 105. Further, the fourth layer 104 defines one outlet channel 138A–138N corresponding to each separation column 161A–161N (defined in the seventh layer 107), with each outlet channel 138A–138N having an optical detection region 139A–139N disposed in a fault-tolerant zig-zag or "Z"-shape. The purpose of this fault tolerant detection segment is to accommodate any anticipated dimensional variation of the outlet channels 138A–138N along the transverse direction to mitigate potential misalignment with an external illumination source and/or detector (not shown).

In addition to the structures described previously, the fifth layer 105 defines a slit 141 disposed between the mixing channel 131 defined in the fourth layer and the enlarged end 152 of a channel segment 151 defined in the sixth layer 106 to assist in mixing mobile phase solvents within the device 100. The fifth layer 105 further defines eight sample injection vias 145A–145N in fluid communication with the sample injection segments 135A–135N defined in the fourth layer 104. Eight column outlet vias 147A–147N are further defined in the fifth layer 105 and in fluid communication with the outlet channels 138A–138N defined in the fourth layer 104.

Two porous materials 150, 160 are disposed between the fifth layer 104 and the sixth layer 105. These materials 150, 160 serve as frits to retain stationary phase material 169 within the separation channels 161A–161N defined in the seventh 107. In other words, the frits 150, 160 permit the passage of liquid solvent, but impede the passage of stationary phase material 169. If the stationary phase material 169 includes packed particulate matter, then the frits 150, 160 preferably have a pore size that is smaller than the particles to be retained. Another porous material 170 is disposed between the outlet ports 118A–118N defined in the first layer 101 and the vias 128A–128N defined in the second layer 102. The function of this porous material 170 is to provide retain pressure (i.e., elevate fluidic backpressure) within the optical detection regions 139A–139N defined in the fourth layer 104 so as to prevent the formation of bubbles therein. Although various materials may be used for the porous materials 150, 160, 170, a preferred material for constructing these elements 150, 160, 170 is a permeable polypropylene membrane such as, for example, 1-mil (25 microns) thickness Celgard 2500 membrane (55% porosity, 0.209×0.054 micron pore size, Celgard Inc., Charlotte, N.C.). This is particularly preferred when the device layers 101–109 are fabricated with a substantially adhesiveless polyolefin material, such as non-biaxially-oriented polypropylene, using direct (e.g. thermal) bonding methods such as discussed herein. Devices 100 constructed according to such methods may be readily capable of withstanding (internal) operating pressures of 10 psi (69 kPa), 50 psi (345 kPa), 100 psi (690 kPa), 500 psi (3450 kPa), or even greater pressures.

The sixth layer 106 of the device 100 defines a channel segment 151 having an enlarged end 152 to promote mobile phase solvent mixing. Further defined in the sixth layer 106 are eight sample injection vias 155A–155N (corresponding to the vias 145A–145N defined in the fifth layer 105) and eight column outlet vias 157A–157N (corresponding to the vias 147A–147N defined in the fifth layer 105).

The seventh layer 107 defines eight parallel separation columns 161A–161N, a transverse channel segment 172, and two medium forked channels 174A, 174B. The eighth layer 108 defines one large forked channel 173 and four small forked channels 176A–176D. The ninth layer 109, which serves to bound the structures in the eighth layer 108 from below, defines only alignment holes 180–181 and apertures 177A–177N to facilitate optical detection. Notably, if additional stiffness or structural rigidity is desired, a thicker bottom layer 109 may be used or the device 100 may be constructed with additional lower layers (not shown) substantially identical to the ninth layer 109.

While channels and other microstructures of various dimensions may be used in a separation device 100, in a preferred embodiment the separation columns 161A–161N each have a nominal width of about 40 mils (about 1 mm), and the downstream channels 138A–138N and associated vias 147A–147N, 118A–118N have widths/diameters of about 25 mils (about 625 microns).

Stationary phase material 169 is preferably added to the device 100 after the various layers 101–109 and porous elements 150, 160, 170 are laminated or otherwise bonded together to form an integral structure. While various types of stationary phase material may be used, preferred types include packed particulate material, and preferred packing methods employ slurry. One preferred slurry includes silica powder having surface chemical groups (e.g., Pinnacle II™ C-18 silica, 5-micron, catalog no. 551071, Restek Corp., Bellefonte, Pa.) and acetonitrile (MeCN), such as in a ratio of 1.00 grams particulate to 500 ml of solvent. Different sizes and types of particulate material may be used. Pressurized slurry may be supplied to the device 100 by way of a solvent inlet port 112. From the solvent inlet port 112 and associated vias 122, the slurry is split to the eight separation channels 161–168 through a microfluidic distribution network that includes an elongate transverse channel segment 172, the large forked channel 173, the intermediate forked channels 174A–174B, and the small forked channels 176A–176D. Upon filling the separation columns 161A–161N, particulate matter within the slurry is prevented from leaving the channels 161A–161N by way of the frits 150, 160, and solvent separated from the slurry emerges from the device 100 through the downstream frit 160, vias 147A–147N, channels 138A–138N, vias 128A–128N, and finally the outlet ports 118A–118N. Preferably, pressurized slurry is added to the device 100 until not only the separation channels 161–168 are filled, but also the forked channels 176A–176D, 174A–174D, 173 and the transverse segment 172 are filled so as to leave a trailing edge of stationary phase material disposed adjacent to the solvent inlet port 112.

In operation of the device 100, a first mobile phase solvent may be supplied to one solvent inlet port 114 and a second mobile phase solvent may be supplied to another solvent inlet port 116. These two solvents meet within the mixing channel 131 adjacent to the slit 141 (defined in the fifth layer 104), after which the two solvents are laminated one atop the other to promote mixing. Preferably, each solvent is supplied by an independently controlled pressure source (e.g., a pump) to permit gradient separation to be performed within the device 100. From the mixing channel 131, the combined solvents flow through a compact composite channel composed of seven (parallel) longitudinal segments 142A–142G defined in the fifth layer 105 alternated with six transverse segments 132A–132F defined in the fourth layer 104 that provide a relatively long channel structure within a compact area. From the last longitudinal channel 142G, the solvent mixture flows into a curved channel 133 leading to a composite splitter including a large forked channel 143, two intermediate channel segments 134A–134B, and four small forked channels 144A–144D that in turn supply the solvent mixture to the sample loading channels 135A–135N upstream of the sample loading ports 110A–110N. The sample loading channels 135A–135N are in fluid communication with the separation columns 161A–161N Preferably, another pressurized solvent stream is supplied to the device 100 through the solvent inlet port 112. This second solvent stream provided through the solvent inlet port 112 helps prevent stationary phase material from unpacking within the separation column, and also helps to ensures that sample plugs injected into the sample loading channels 135A–135H flow exclusively through the downstream portions 161B–168B of the separation channels 161–168.

After the stationary phase material 169 is fully wetted with solvent, samples may be added to the device 100 through the sample ports 110A–110N and 111A–111N. Preferably, solvent flow is interrupted and the device is temporarily depressurized (e.g., by disengaging a removable mechanical seal (not shown) from the sample loading ports 110A–110N, 111A–111N) to permit the samples to be loaded. Two sample ports (e.g., 110A, 111A) correspond to each sample loading segment (e.g., 135A) of the eight sample loading segments 135A–135N defined in the third layer 103. Preferably, different samples are provided to each upstream port (110A–110N) and each sample flows within a portion of a sample loading segment 135A–135N to emerge through the downstream port 111A–111N so as to define a sample plug of a repeatable volume in each sample loading segment between the upstream port (e.g., port 110A) and downstream port (e.g., 111A). After the samples are loaded, the sample loading ports 110A–110N, 111A–111N are preferably re-sealed (e.g., by disengaging a removable mechanical seal (not shown)) and solvent flow through solvent ports 112, 114, 116 is re-initiated. The solvents supplied into the sample loading segments 135A–135N from the sample inlet ports 114, 116 sweep the sample plugs onto the separation columns 161A–161N where they are eluted.

Applicants have constructed and tested microfluidic separation devices according the design of the device 200 illustrated in FIGS. 1A–1C, In operation, mobile phase solvent pressurized with a conventional HPLC pump was supplied to the device 200, where the packed separation columns and porous materials provided a fluidic backpressure of about three hundred fifty psi (about 2410 kPa). No bubbles were observed in the detection regions 139A–139. In previous but similar designs lacking the downstream porous membrane 170, bubble formation in detection regions downstream of the separation columns 161A–161N was frequently observed. Thus, it is believed that the presence of the porous membrane 170 supplied sufficient backpressure to elevate the pressure within the optical detection regions 139A–139N to as to suppress bubble formation. As is evident from FIGS. 1A–1C, the porous membrane 170 is highly compact, particularly compared to the use of capillary tubing or conventional backpressure regulators. Additionally, the ability of the porous membrane 170 to span across the outlet of all (eight) separation columns 161A–161N simplifies manufacture of the device 100, since cutting and alignment of only a single element 170 is required.

Another method for generating a backpressure region within a microfluidic channel is to chemically manufacture a porous monolithic region in place. A porous monolithic region composed of a macroporous crosslinked material will have a permanent porous structure providing resistance to fluid flow (e.g., backpressure when pressurized from one end). The resulting flow resistance can be controlled by (1) varying the pore size, and/or (2) varying the length of the porous region to be encountered by the fluid. Smaller pores and/or longer porous regions resist fluid flow more than larger pores and/or shorter porous regions.

One method of chemically manufacturing such a flow resistance region involves polymerizing a solution in a microfluidic channel. Polymerization of solutions to yield porous regions are well-known in the arts of capillary electrochromatography, where such porous materials are used as stationary phase to effect separation of various analytes. Typically, a mold is filled with a "pre-monolith" mixture comprised of a cross-linking monomer, comonomers, an initiator, and a progenic solvent. Upon polymerization, a porous monolith that conforms to the shape of the mold is obtained. Various activation means, including thermal and photochemical means, may be used with such a process. Typically, such a solution is polymerized in pre-treated glass capillary tubes or glass channels. The pre-treatment functionalizes the silica so that the ensuing polymer will be covalently linked to the wall.

Pore structure of the monolith is sensitive to very small changes in the composition of the progenic solvent (which may be solvating or non-solvating in nature). A carefully chosen ternary solvent mixture can be used to allow for fine control of the porous properties of the monolithic column. Pore size may also be controlled by addition of a suitable chain transfer agent. Additionally, the following parameters may be used to control the porous properties of the resulting monolithic material: the percentage of a cross-linker, reaction temperature, and initiator concentration.

Figure 2A:
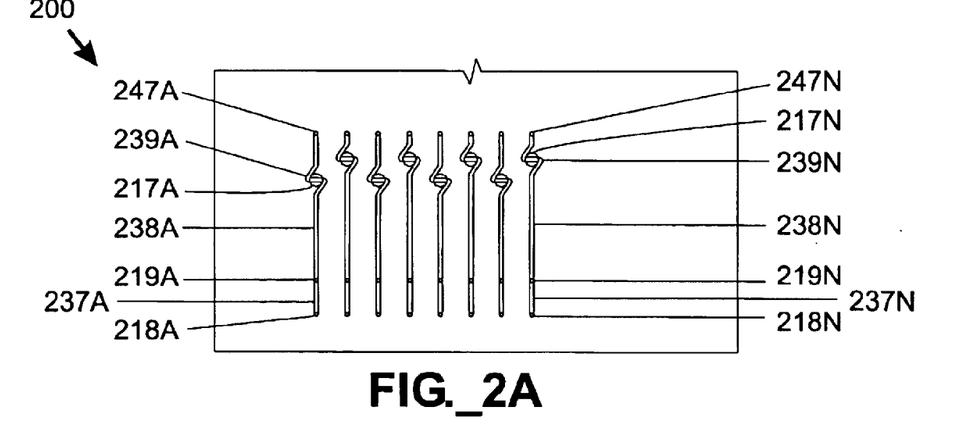
FIG. 2A is a simplified top view of a portion of a pressure-driven microfluidic separation device adapted to retain monolithic porous regions downstream of optical detection regions, the view including the optical detection regions but omitting other elements for clarity.

Referring generally to FIGS. 2A–2D, monolithic flow resistance regions may be generated within a pressure-driven microfluidic separation device using a photomask and an activation source. FIG. 2A provides a simplified view of a portion of a pressure-driven microfluidic separation device 200 similar to the device 100 discussed previously, with the addition of a short channel segment 237A–237N corresponding to each channel segment 238A–238N downstream of the optical detection regions 239A–239N. Notably, upstream separation columns, frits, and other structures similar to those provided in FIGS. 1A–1B are omitted for clarity from FIGS. 1C, 2A but are preferably provided. Referring back to FIG. 2A, the illustrated portion of the device 200 includes eluate vias 247A–247N (intended to be downstream of separation columns (not shown) such as illustrated in FIGS. 1A–1B); channel segments 238A–238N including Z-shaped detection regions 239A–239N; vias 219A–219N; short channel segments 237A–237N; and outlet ports 218A–218N. The short channel segments 237A–237N are preferably defined in a different device layer than the upstream segments 238A–238N, with fluid communication between corresponding segments 238A–238N, 237A–237N made by way of vias 219A–219N. Preferably, the vias 219A–219N are slightly smaller in diameter than the width of the upstream channel segments 238A–238N so as to retain porous polymeric monoliths in the upstream segments 238A–238N.

Figure 2B:
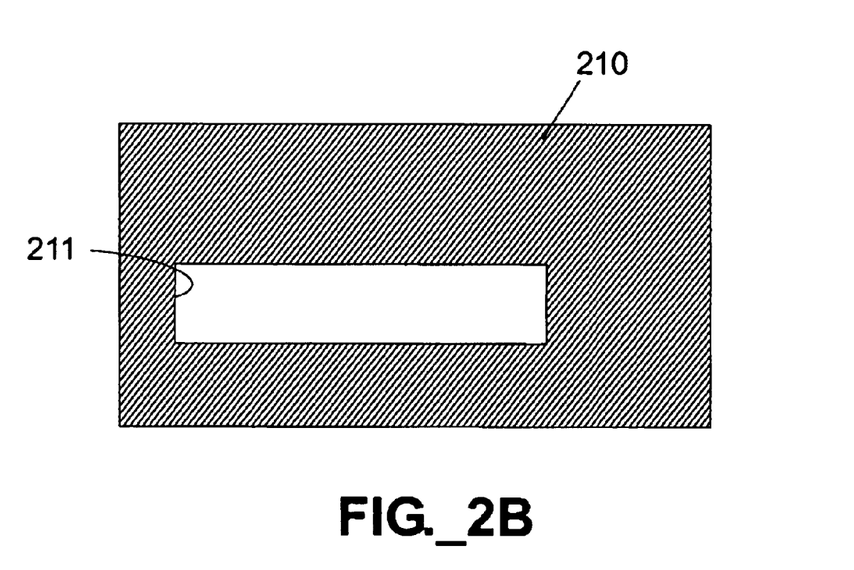
FIG. 2B is a top view of a photomask useful for preparing monolithic porous regions in microfluidic channels.
Figure 2C:
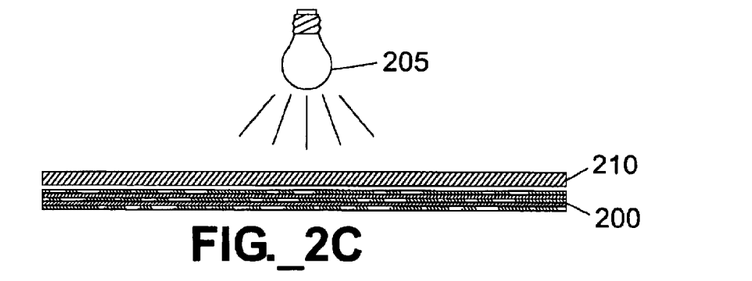
FIG. 2C is a side schematic view of a radiation source supplying radiation to selected regions of a microfluidic separation device according to FIG. 2A through a photomask according to FIG. 2B.
Figure 2D:
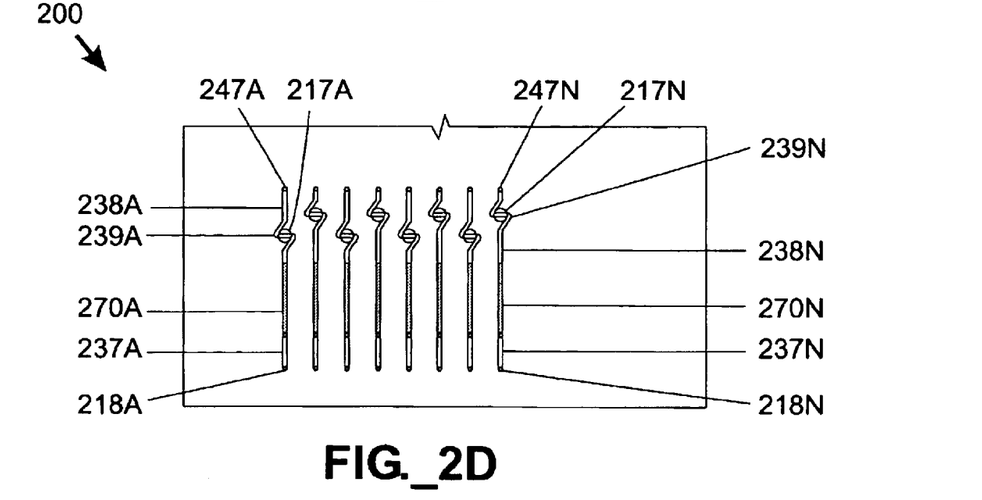
FIG. 2D provides the same simplified top view as FIG. 2A of a portion of a separation device, but with the device including multiple monolithic porous backpressure regions (downstream of the optical detection regions) prepared with the photomask of FIG. 2B.

Starting with the device 200 illustrated in FIG. 2A, pre-monolith mixture is supplied to the device 200 through the outlet ports 218A–218N to fill the channel segments 238A–238N. Separately, a photomask is prepared to overlay the device 200 containing the pre-monolith. An example of a representative photomask 210 is provided in FIG. 2B. The photomask 210 shown in FIG. 2B is fabricated with an opaque, preferably absorptive material defining a single wide window 211. A side view of a photomask (e.g., mask 210) applied to a microfluidic splitting device (e.g., device 200) containing a pre-monolith mixture is illustrated in FIG. 2C. A light source 205 supplies light, preferably ultraviolet light, to any region of the microfluidic device 200 left uncovered by the window 211 in the photomask 210 so as to locally polymerize the mixture within the microfluidic channels 138A–138N to form porous regions or monoliths 270A–270N (as shown in FIG. 2D) downstream of the optical detection regions 139A–139N. Following the polymerization step, any remaining unpolymerized pre-monolith mixture may be rinsed from the device 200. Following polymerization of the porous regions or monoliths 270A–270N, sufficient backpressure may be generated to prevent bubble formation in the optical detection regions 239A–239N. As will be recognized by one of ordinary skill in the art, the desired degree of backpressure may be adjusted by: altering the pre-monolith mixture to change the porosity of the resulting monolith; adjusting the dimensions of the channel segments 238A–238N; and/or adjusting the size of each monolithic porous region, such as by changing the size of the window 211 in the photomask 210.

Applicants have prepared porous polymeric monoliths in polypropylene microfluidic channels similar in character to the channels 238A–238N provided in the device 200 illustrated in FIG. 2D. All of the starting materials used for the procedure were obtained from Sigma-Aldridge Corp. (Milwaukee, Wis.) and used as received. First, a casting solvent was prepared by mixing ethanol (20%), MeCN (60%), and 5 mM phosphate buffer, pH 6.8 (20%). Next, 5 mg of 2,2' azobisisobutyronitrile (AIBN) radical initiator, 297 microliters of 1,3 butanediol acrylate (BDDA), 685 microliters of butylacrylate, and 3 microliters of (Dow Corning) z-6030 adhesion promoter were dissolved in 2 ml of the casting solvent. The resulting mixture was sonicated for 5 minutes. The mixture was then drawn into a syringe and injected into a microfluidic channel. A mask was then applied to the microfluidic device to permit localized light exposure. Next, the masked microfluidic device was exposed to ultraviolet radiation (a 365 nm, 1 J/cm source was used) for approximately 1 hour without any additional heating. An opaque white-colored porous monolith resulted in the microfluidic channel. The channels were subsequently washed with acetonitrile to flush out any unreacted monomer solution remaining in the channel behind the masked regions. The resulting monolith provided measurable resistance to fluid flow.

In another example, a monolithic ion-exchange column may be fabricated with a monomer solution of about 2.5 ml of 50-millimolar neutral pH sodium phosphate, 0.18 grams of ammonium sulfate, 44 microliters of diallyl dimethlyammonium chloride, 0.26 grams of methacrylamide, and 0.35 grams of piperazine diacrylamide. Further specific recipes for monolithic columns are provided, for example, in Ngola, S. M., et al., Conduct-as-cast polymer monoliths as separation media for capillary electrochromatography, Anal. Chem., 2001, Vol. 73, pp. 849–856; in Shediac, R., et al., Reversed-phase Electrochromatography of amino acids and peptides using porous polymer monoliths, J. Chrom. A., 2001, vol. 925, pp. 251–263; and in Ericson, C., et al., Electroosmosis- and pressure-driven chromatography in chips using continuous beds, Anal. Chem., 2001, vol. 72, pp. 81–87, each of which are incorporated herein by reference.

One enhancement to the foregoing method for polymerizing a solution in a polypropylene channel includes surface treatment of the polypropylene to promote adhesion between the monolith and the channel surfaces. Preferable treatment methods include corona discharge, flame treatment, vacuum plasma (utilizing nitrogen and oxygen); air plasma (using atmospheric air), fluorination, addition of 0.025% malic acid to polypropylene; infrared laser (2% carbon black) treatment; AgII electrolysis; and chromic acid treatment. Each of these methods may provide different degrees of surface modification. Monoliths polymerized in treated channels are expected to provide greater flow resistance as compared to monoliths prepared in untreated channels. For further details on such surface treatment methods, see "Characterisation and Comparison of Surface Modification on Homopolymer Polypropylene" M. D. Green, F. J. Guild and R. D. Adams, a conference paper published in the proceedings of the 23rd Annual Meeting of the Adhesion Society, Myrtle Beach, S.C., USA. Feb. 20–23, 2000 (pg 541–543).

In an alternative embodiment, thermal conditioning of a sol-gel solution may be used to generate flow resistance regions within microfluidic devices. Generally, a sol-gel process involves the transition of a system from a liquid "sol" (mostly colloidal) to a solid "gel" phase for making ceramic or glass materials. The starting materials used in preparing the "sol" are usually inorganic or metal salts or metal organic compounds such as metal alkoxides. In a typical sol-gel process, the precursor is subjected to a series of hydrolysis and polymerization reactions to form a colloidal suspension, or a "sol." When the "sol" is cast into a mold, a wet "gel" will form. With further treatment, such as heating and drying, the "gel" is converted into ceramic or glass articles.

As applied to a microfluidic device, a thermally-activated sol-gel solution may be flowed into one or more channels or regions and then converted to solid or "gel" phase to serve as flow resistance regions. For example, a sol-gel solution may be prepared by mixing tetramethyl orthosilicate (TMOS), octadecyl trimethoxysilane (C-18TMOS); phenyldimethylsilane (PheDMS), and trifluoroacetic acid (TFA). Upon the application of heat to the solution contained in the device, a porous sol-gel region results. For further details on one example of preparation sol-gels, see Hayes, J. D., Malik, A., "Sol-Gel Monolithic Columns With Reversed Electroosmotic Flow for Capillary Electrochromatography," Anal. Chem. 2000, Vol. 72, pp. 4090–4099, which is incorporated herein by reference.

Figure 3:
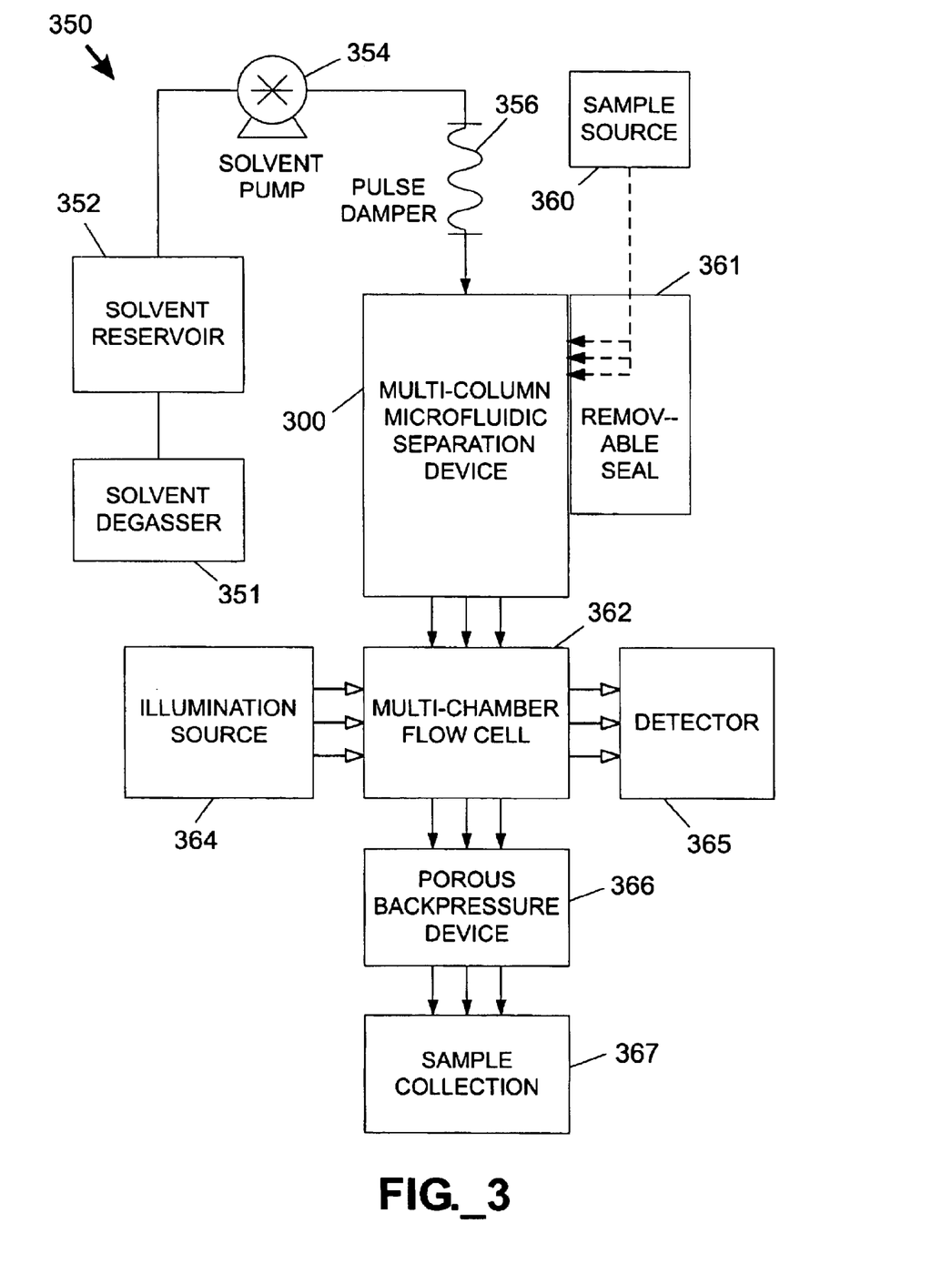
FIG. 3 is a schematic showing various components of a pressure-driven analytical system adapted to perform liquid chromatography with a microfluidic separation device having at least one microfluidic separation column, the system including at least one optical detection region downstream of the at least one separation column, and at least one porous backpressure device disposed downstream of the at least one optical detection region.

In another embodiment, a pressure-driven analytical system includes a porous backpressure device that may or may not be integrated with a microfluidic separation device having one or more separation columns. For example, FIG. 3 is a schematic illustrating various components of a pressure-driven analytical system adapted to perform liquid chromatography. Various standard HPLC components, such as a solvent reservoir 352, a solvent degasser 351, one or more solvent pumps 354, and pulse damper 356 may be used. A multi-column microfluidic device 300 disposed downstream of the mobile phase solvent supply system (e.g., including components 351, 352, 354, 356) receives samples from a sample source 360. Preferably, fluid connections to the microfluidic device 300 are made with a removable seal 361, which may include one or more gasketed surfaces or O-rings sealed with compressive forces. An external flow cell 362 may be used to provide optimal optical properties. For example, a multi-chamber flow cell 362, such as disclosed in commonly assigned U.S. patent application Ser. No. 10/282,392 filed Oct. 29, 2002 (hereby incorporated by reference as if fully set forth herein), may be used. Alternatively, multiple discrete conventional flow cells may be used. In a further alternative, as described previously herein, optical detection regions may be integrated into a column-containing microfluidic device. An illumination source 364 and optical detector 365 are provided in fluid communication with the flow cell 362 or other optical detection region (e.g., regions 139A–139N, 239A–239N described above). Remote placement of the illumination source 364 and optical detector 365 relative to the flow cell or other optical detection region 362 may be aided with fiber optic elements (not shown). Downstream of the flow cell 362, a porous backpressure device 366 elevates the fluid pressure within the flow cell 362, thus suppressing bubble formation therein. Finally, the separated species are supplied to a sample collector 367, where they may be further analyzed by another technique (e.g., mass spectrometry), stored, or discarded.

Returning to the porous backpressure device 366, such a device 366 may include one or more porous membranes, porous monoliths, or other types of porous regions to elevate fluid pressure within the flow cell. In one embodiment, the porous backpressure device 366 includes a substantially planar porous material sandwiched between device layers containing a first aperture and a second aperture in fluid communication with a flow cell or optical detection region. In another embodiment, the porous backpressure device 366 is removably coupled to the analytical system 350 to permit the device 365 to be changed if necessary, such as to avoid cross-contamination with future sample runs or to optimize system performance. In another embodiment, the porous backpressure device 366 is integrated with the separation device 300, with fluid connections both to and from the flow cell 362 being provided. Such integration may be desirable to render both the separation device 300 and backpressure device 366 easily disposable after a desired number of uses.

It is to be appreciated that the foregoing description of the invention has been presented for purposes of illustration and explanation and is not intended to limit the invention to the precise manner of practice herein. It is to be appreciated, therefore, that changes may be made by those skilled in the art without departing from the spirit of the invention, and that the scope of the invention should be interpreted with respect to the following claims and their legal equivalents.

What is claimed is:

1. A microfluidic analytical device comprising:
a microfluidic separation column containing stationary phase material and adapted to perform a pressure-driven chromatographic separation process;
an optical detection region disposed downstream of the microfluidic separation column, the optical detection region being substantially free of stationary phase material and being bounded by at least one substantially optically transmissive material; and
a substantially planar porous membrane disposed downstream of the optical detection region, the porous membrane permitting liquid flow therethrough at an operating pressure.

2. The device of claim 1 wherein the device is substantially planar and comprises a plurality of substantially planar device layers.

3. The device of claim 1 wherein the membrane is a permeable polyolefin membrane.

4. The device of claim 1 wherein the plurality of device layers comprises adhesiveless polymeric layers that are interpenetrably bound together to form a substantially sealed microstructure.

5. The device of claim 4 wherein each device layer of plurality of device layers is substantially metal-free.

6. The device of claim 2 wherein the plurality of substantially planar device layers includes a plurality of stencil layers.

7. The device of claim 6 wherein the porous membrane is disposed between at least two stencil layers of the plurality of stencil layers.

8. The device of claim 1 wherein the stationary phase material includes packed particulate matter.

9. The device of claim 1 wherein the microfluidic analytical device is adapted to withstand an internal pressure of at least about 100 psi and remain substantially sealed.

10. A microfluidic analytical device comprising:
- a plurality of microfluidic separation columns each containing stationary phase material;
- a plurality of optical detection regions, each optical detection region of the plurality of optical detection regions being disposed downstream of and in fluid communication with a different microfluidic separation column of the plurality of separation columns, being substantially free of stationary phase material, and being bounded by at least one substantially optically transmissive material; and
- at least one porous membrane disposed downstream of the plurality of optical detection regions, the at least one porous membrane permitting liquid flow therethrough at an operating pressure.

11. The device of claim 10, further comprising a fluidic distribution network in fluid communication with the plurality of microfluidic separation columns.

12. The device of claim 10 wherein the device is substantially planar and comprises a plurality of substantially planar device layers.

13. The device of claim 10 wherein the plurality of device layers comprises adhesiveless polymeric materials that are interpenetrably bound together to form a substantially sealed microstructure.

14. The device of claim 13 wherein each device layer of the plurality of device layers is substantially metal-free.

15. The device of claim 12 wherein the plurality of device layers includes a plurality of stencil layers.

16. The device of claim 15 wherein the at least one porous membrane is disposed between at least two stencil layers of the plurality of stencil layers.

17. An analytical system comprising:
- the device of claim 10;
- a fluidic distribution network in fluid communication with the plurality of microfluidic separation columns;
- a common mobile phase supply source in fluid communication with the plurality of microfluidic separation columns through the fluidic distribution network;
- at least one illumination source in optical communication with the plurality of optical detection regions; and
- at least one optical detector in optical communication with the plurality of optical detection regions.

18. A microfluidic device comprising:
- a plurality of substantially planar device layers defining a separation region, an impedance region, and an optical detection region disposed in a fluid flow path between the separation region and the impedance region, the optical detection region being substantially free of stationary phase material and being bounded along at least one surface by a substantially optically transmissive material; and
- a substantially planar porous membrane disposed between the first aperture and the second aperture, with the porous membrane permitting liquid flow therethrough and being adapted to permanently elevate the backpressure within the optical detection region.

19. The device of claim 18, further comprising at least one microfluidic separation column adapted to perform pressure-driven liquid chromatography, the separation column being disposed upstream of the optical detection region.

20. The device of claim 18 wherein the plurality of substantially planar device layers includes a plurality of stencil layers.

21. A liquid chromatography system comprising:
- a plurality of separation columns adapted to perform pressure-driven liquid chromatographic separation;
- an illumination source;
- an optical detector;
- a plurality of optical detection regions disposed downstream of the plurality of separation columns, each optical detection region of the plurality of optical detection regions being in fluid communication with a different separation column of the plurality of separation columns, and each optical detection region being in optical communication with the illumination source and optical detector; and
- at least one porous membrane disposed downstream of the plurality of optical detection regions and in fluid communication with the plurality of optical detection regions, the at least one porous membrane being adapted to elevate the backpressure within the plurality of optical detection regions.

22. The system of claim 21, further comprising a mobile phase supply system.

23. The system of claim 21 wherein each separation column of the plurality of separation columns is microfluidic.

* * * * *

UNITED STATES PATENT AND TRADEMARK OFFICE
CERTIFICATE OF CORRECTION

PATENT NO. : 7,010,964 B2 Page 1 of 1
APPLICATION NO. : 10/697923
DATED : March 14, 2006
INVENTOR(S) : Christoph D. Karp et al.

It is certified that error appears in the above-identified patent and that said Letters Patent is hereby corrected as shown below:

on the title page item [56],

In the References Cited: U.S. Patent Documents section, page 2, first column, add -- 6,623,860 B1 9/2003 Hu et al. .................. 428/411.1 --

Column 7, line 20, "ports 111A-110N" should be -- ports 110A-110N --

Column 12, line 39, "1 J/cm source" should be -- 1 J/cm$^2$ source --

Signed and Sealed this

Twenty-second Day of August, 2006

JON W. DUDAS
*Director of the United States Patent and Trademark Office*